(12) United States Patent
Kim et al.

(10) Patent No.: US 12,130,220 B2
(45) Date of Patent: Oct. 29, 2024

(54) BIOSENSOR USING EXCEPTIONAL POINT

(71) Applicant: DAEGU GYEONGBUK INSTITUTE OF SCIENCE AND TECHNOLOGY, Daegu (KR)

(72) Inventors: Chil Min Kim, Seoul (KR); Jin Hyeok Ryu, Daegu (KR); Chang Hwan Yi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 284 days.

(21) Appl. No.: 17/634,637

(22) PCT Filed: Mar. 19, 2020

(86) PCT No.: PCT/KR2020/003736
§ 371 (c)(1),
(2) Date: Feb. 11, 2022

(87) PCT Pub. No.: WO2021/029510
PCT Pub. Date: Feb. 18, 2021

(65) Prior Publication Data
US 2022/0326134 A1 Oct. 13, 2022

(30) Foreign Application Priority Data
Aug. 12, 2019 (KR) .................. 10-2019-0098262

(51) Int. Cl.
*G01N 15/06* (2024.01)
*G01N 15/01* (2024.01)
*G01N 15/075* (2024.01)

(52) U.S. Cl.
CPC ......... *G01N 15/0606* (2013.01); *G01N 15/01* (2024.01); *G01N 15/075* (2024.01)

(58) Field of Classification Search
CPC .... G02F 1/365; G02F 2203/15; H01S 3/0604; H01S 3/082; H01S 3/176; H01S 3/063;
(Continued)

(56) References Cited

U.S. PATENT DOCUMENTS 7,612,887 B2* 11/2009 Choi .................. G02B 6/12007
385/12
2013/0309135 A1* 11/2013 Park ....................... G01N 21/17
422/69
(Continued)

FOREIGN PATENT DOCUMENTS

| KR | 20070062562 | 6/2007 |
| KR | 20130108051 | 10/2013 |
| KR | 20140112275 | 9/2014 |

OTHER PUBLICATIONS

KIPO, PCT Search Report of PCT/KR2020/003736 dated Jul. 2, 2020.

*Primary Examiner* — Tarifur R Chowdhury
*Assistant Examiner* — Roberto Fabian, Jr.
(74) *Attorney, Agent, or Firm* — LEX IP MEISTER, PLLC

(57) ABSTRACT

A biosensor using an exceptional point is disclosed. A biosensor according to one embodiment of the present disclosure includes: a biosensing unit configured to output wavelength-separated optical signals from destruction of an exceptional point resulting from attachment of biomolecules; a detection unit configured to convert the wavelength-separated optical signals into wavelength-separated electrical signals; an analysis unit configured to measure a beat frequency resulting from the wavelength-separated electrical signals; and a determination unit configured to determine a wavelength difference resulting from the beat frequency, thereby determining the amount of the biomolecules therefrom.

8 Claims, 14 Drawing Sheets

(58) Field of Classification Search
CPC ..... H01S 5/1071; H01S 3/0627; B82Y 20/00; G01N 15/1434; G01N 2015/0038; G01N 2015/0046; G01N 2015/0053; G01N 2015/1486; G01N 2021/655; G01N 21/7746; G01N 15/0606; G01N 15/075; G01N 15/1429; G01N 15/1484; G01N 2021/7789; G01N 33/49; G01N 33/487; G01N 33/483

See application file for complete search history.

(56) References Cited

U.S. PATENT DOCUMENTS

| | | | | |
|---|---|---|---|---|
| 2015/0295379 | A1* | 10/2015 | Ozdemir | H01S 3/10092 |
| | | | | 359/337.4 |
| 2018/0261977 | A1* | 9/2018 | Feng | H01S 5/1228 |
| 2018/0306696 | A1* | 10/2018 | Ozdemir | G01N 21/7746 |

* cited by examiner

BIOSENSOR USING EXCEPTIONAL POINT

TECHNICAL FIELD

The present disclosure relates to a biosensor using an exceptional point.

BACKGROUND ART

In order to diagnose diseases such as cancer, thorough efforts other than traditional biopsy have recently been focused on the detection of biomolecules in blood. This type of technique, also known as liquid biopsy, is the sampling and analysis of blood to diagnose disease.

Unlike traditional biopsies adapted to sample tumor cells from patients through surgery, such a liquid biopsy has attracted intensive attention because it can sample blood with only a syringe, which may be the minimum surgical tool.

However, blood retains a very small content of target molecules to be detected. Sometimes, for example, even though blood is sampled, circulating cancer cells could not be detected therein because they amount merely to 10 or less in 7.5 mL of blood. As for exosomes, their number is very large, amounting to $10^6$ per milliliter, but exosomes are difficult to detect due to their small size and low molecular weight.

Nonetheless, active studies on liquid biopsy are ongoing because they can be applied to early diagnosis of diseases, customized cancer diagnosis such as prognosis observation, clinical decision, and treatment monitoring in cancer patients, or precision medicine as well as being used for development of new drug development such as for new drug screening, target discovery, etc.

For such a liquid biopsy, biomolecules which are present in trace amounts or have very small molecular weights must also be detected. To this end, many biosensors have been developed.

Biosensors are largely classified into two detection types: detection of protein biomarkers through antigen/antibody interactions and detection of DNA and RNA through interaction between complementary sequences.

Protein biomarker detection through antigen/antibody interaction takes advantage of various signal amplifications to allow for detection of biomarkers even if they are present at a trace level.

In this regard, enzyme-linked immunosorbent assay (ELISA) is used as the absolute reference for quantitative analysis of proteins (antigen and antibody both). However, this assay, which is a multi-stage analysis technique, is labor intensive and is unable to detect a concentration of 1 ng/mL or less due to the very poor sensitivity thereof although fluorescent and luminescent signals are amplified once with an enzyme.

A lateral flow immunoassay, also known as immunochromatography system, is frequently used because of its ability to perform a rapid analysis at low cost. However, the application of this method is limited to the detection of chorionic gonadotrophin (hCG) which is a target produced at a very high concentration in pregnancy, due to its very low sensitivity (LOD (limit of detection) of commercially available kit: 1-5 ng/mL).

An electrochemical immunosensor has been suggested in order to enhance LOD to 10-100 fg/mL in protein biomarkers, but is short in lifespan and works only at a narrow range of temperatures, thus having the problem of ensuring reliability with the resultant limitations imparted into the applications thereof.

Detection methods using nanobeads, surface plasmon resonance (SPR), and surface enhanced Raman spectroscopy (SERS) each have a limit of detection of as high as 1 pg/mL, but is difficult and complicated in terms of usage.

As for the biosensor directing toward the detection of DNA and RNA, its target may include DNA isolated from cells (cell-free DNA: cfDNA) and endoplasmic reticulum RNA. For detection, the number of DNA copies is increased by polymerase chain reaction (PCR), or next-generation sequencing (NGS) technology is employed.

These technologies can detect even one nucleic acid molecule, but requires expensive sequencers, well-trained operators, and a long operation time. Although drastically reduced in the last five years, the cost for detection by these technologies still amounts to 100 dollars or more per sample (exclusive of price of the sequencer).

In spite of development of biosensors for liquid biopsies, low sensitivity, restricted specificity, labor-intensive and time-consuming work, and high cost still, on the whole, remain as barriers against the clinical application of the biosensors.

Development was also made of a biomolecule detecting method using a ring microresonator. This method takes advantage of the phenomenon that when a biomolecule adheres to the surface of the ring resonator, the wavelength is shifted in a whispering gallery mode around the ring resonator.

According to this method, when a biomolecule is attached to the surface of the ring microresonator, the mean refractive index is changed, and the total length of the resonator is increased by the biomolecule, which causes the production of a gallery mode fitting to the changed length of the resonator, with the consequent shift of wavelengths. This method succeeded to detect interleukin-II at a concentration of down to 100 attoM, but there is still a need of a system capable of detecting biomolecules at lower concentrations.

DISCLOSURE OF INVENTION

Technical Problem

An aspect of the present disclosure is to provide a biosensor capable of quantitatively precisely detecting a target biomolecule by taking advantage of the phenomenon that when a system including a microresonator with an exceptional point, a microresonator laser, or combined optical waveguides is coupled with a biomolecule, the exceptional point is destroyed to split the wavelengths.

Solution to Problem

To solve the above technical problems, a biosensor of one embodiment of the present disclosure may include: a biosensing unit configured to output wavelength-separated optical signals from destruction of an exceptional point resulting from attachment of biomolecules; a detection unit configured to convert the wavelength-separated optical signals into wavelength-separated electrical signals; an analysis unit configured to measure a beat frequency by the wavelength-separated electrical signal; and a determination unit configured to determine the wavelength difference resulting from the beat frequency, thereby determining the amount of the biomolecules therefrom.

In one embodiment of the present disclosure, the biosensing unit may include: a first microresonator having a circular top surface having a first radius; and a second microresonator having a circular top surface having a second radius, the second microresonator being spaced apart from the first microresonator by a predetermined distance and coupled to the first microresonator to form an exceptional point.

In one embodiment of the present disclosure, the biosensing unit may include: a first microresonator having a circular top surface; a second microresonator having a circular cross-section and a radius decreasing from the top to the bottom thereof; a moving unit configured to move the first microresonator up and down and left and right; and a control unit configured to adjust the radius of the second microresonator and the distance between the first and the second microresonator by the movement of the first microresonator so as to form an exceptional point by the coupled first and second microresonators.

In one embodiment of the present disclosure, the angle formed by the vertical plane and the side surface of the second microresonator may be within 20 degrees.

In one embodiment of the present disclosure, the biosensing unit may include a single microresonator which is deformed to be mirror-symmetrical or asymmetrical so as to form an exceptional point.

In one embodiment of the present disclosure, the biosensing unit may include a plurality of optical waveguides which form an exceptional point.

In one embodiment of the present disclosure, the first and the second microresonator may be formed of silica or titanium dioxide ($TiO_2$).

In one embodiment of the present disclosure, the first and the second microresonator may be formed of a laser medium.

The biosensor according to one embodiment of the present disclosure may further include a signal input unit configured to input an electrical signal for generating a new beat frequency generated by subjecting the signal to beating with the beat frequency.

Advantageous Effects of Invention

The present disclosure as described above detects a wavelength difference in light separated due to destruction of an exceptional point, thereby enabling detection of a target biomolecule having extremely high sensitivity.

BEST MODE FOR CARRYING OUT THE INVENTION

Figure 1:
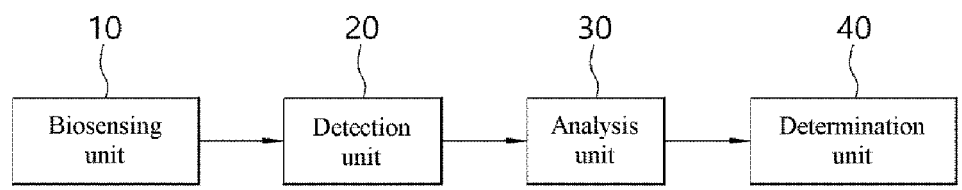
FIG. 1 is a block diagram showing a schematic configuration of a biosensor according to one embodiment of the present disclosure.

To fully understand the configuration and effect of the present disclosure, preferred embodiments of the present disclosure will be described with reference to the accompanying drawings. However, the present disclosure is not limited to the embodiments disclosed below and may be embodied in various forms and various modifications may be applied thereto. The description of the present embodiment is provided so that the disclosure will be complete and will be fully convey the scope thereof to those of ordinary skill in the art to which the present disclosure belongs. In the accompanying drawings, elements are enlarged in size than actual for convenience of description, and ratio of each element may be exaggerated or reduced.

Terms such as 'first' and 'second' may be used to describe various elements, but the elements should not be limited by the above terms. The above term may be used only for the purpose of distinguishing one element from another element. For example, without departing from the scope of the present disclosure, a 'first element' may be termed a 'second element', and similarly, a 'second element' may also be termed a 'first element'. In addition, the singular forms include the plural forms unless the context clearly indicates otherwise. Unless otherwise defined, terms used in the embodiments of the present disclosure may be interpreted as meanings commonly known to those of ordinary skill in the art.

Hereinafter, a physical law of an exceptional point applied to a biosensor of one embodiment of the present disclosure, which is formed in the non-Hermitian physical system, will be described, and a biosensor using the same according to one embodiment of the present disclosure will be described.

The exceptional point is a unique phenomenon that occurs in the non-Hermitian quantum mechanical system and refers to a point at which two eigenvalues are fused to one. At this time, two eigenfunctions corresponding to the two eigenvalues are also fused to one and thus the number of eigenfunctions is also one.

The fused eigenfunction reacts sensitively to external perturbations, and this sensitivity causes the fused eigenfunction to be separated again. When the eigenfunction is separated, the eigenvalue is also separated, which is called mode separation.

To explain this, a phenomenon occurring in a circular resonator will be described first. Since the circular resonator is symmetrical, the circular resonator has only one eigenvalue that satisfies the same quantum numbers while having two eigenfunctions satisfy one eigenvalue. This means that eigenvalues are degenerate into one.

This may be expressed $$H_0 = \begin{pmatrix} E_0 & 0 \\ 0 & E_0 \end{pmatrix}$$

in Hamiltonian terms. Here, all the diagonal components are $E_0$ and thus are equal, and all the off-diagonal components are given as 0. Therefore, all eigenvalues of the Hamiltonian are $E_0$, and thus the number of eigenvalues is one.

At this time, the number of eigenfunctions is two in a mathematical principle, which is said to be degenerate, and this state is called a diabolic point.

If the symmetry of the resonator is broken and thus turns into mirror-symmetry, the diabolic point is broken to be divided into an even mode and an odd mode. Accordingly, the number of eigenfunctions and the number of eigenvalues are both two. If a Hamiltonian that breaks the symmetry is $$H_1 = \begin{pmatrix} \delta & V \\ V^* & \delta \end{pmatrix},$$

the total Hamiltonian becomes $$H' = H_0 + H_1 = \begin{pmatrix} E_0 & 0 \\ 0 & E_0 \end{pmatrix} + \begin{pmatrix} \delta & V \\ V^* & \delta \end{pmatrix} = \begin{pmatrix} E_0 + \delta & V \\ V^* & E_0 + \delta \end{pmatrix}$$

which is obtained by combining the Hamiltonian with the original Hamiltonian. In this case, the eigenvalue is $\lambda_\pm = E_0 + \delta \pm \sqrt{VV^*} = E_0 + \delta \pm |V|$. That is, the number of eigenvalues is two and the number of eigenfunctions resulting therefrom is also two. Here, $\delta$ indicates the change in eigenvalue according to the change in a length of the resonator, and $V$ and $V^*$ indicate perturbations that break the symmetry of the circular resonator.

If another perturbation breaking the symmetry enters the resonator formed in mirror-symmetry, this perturbation may be called $$H_2 = \begin{pmatrix} \gamma & U_1 \\ \alpha U_2 & \gamma \end{pmatrix}$$

a Hamiltonian term. Considering even this case, the total Hamiltonian may be represented as $$H = H_0 + H_1 + H_2 = \begin{pmatrix} E_0 & 0 \\ 0 & E_0 \end{pmatrix} + \begin{pmatrix} \delta & V \\ V^* & \delta \end{pmatrix} + \begin{pmatrix} \gamma & U_1 \\ \alpha U_2 & \gamma \end{pmatrix} = \quad \text{[Equation 1]}$$
$$\begin{pmatrix} E_0 + \delta + \gamma & V + U_1 \\ V^{*+} \alpha U_2 & E_0 + \delta + \gamma \end{pmatrix}$$

The off-diagonal components in the last term of Equation 1 above are $V^*+\alpha U_2$ and $V+U_1$, and when one of the off-diagonal components becomes 0, an exceptional point is formed. In this case, the eigenvalue is $E_0+\delta+\gamma=O$ and thus the number thereof is one.

A case in which $V^*+\alpha U_2$ is 0, a Hamiltonian is $$H = \begin{pmatrix} E_1 & \beta \\ 0 & E_1 \end{pmatrix},$$

and a case in which V+U is 0, the Hamiltonian is $$H = \begin{pmatrix} E_1 & 0 \\ \beta' & E_1 \end{pmatrix}.$$

These cases are called an exceptional point, and in both cases, the eigenvalues are fused to one value and the eigenfunctions are also fused to one. Here, and $E_1 = E_0+\delta+\gamma$, $\beta'=V^*+\alpha U_2$, and $\beta=V+U_1$. These cases are different from the diabolic point with one Hamiltonian eigenvalue and two eigenfunctions in the circular resonator. Therefore, the exceptional point has different characteristics from the diabolic point.

If a biomolecule is bound to the exceptional point, a perturbation arises. If a Hamiltonian of the perturbation is $$H_p = \begin{pmatrix} 0 & \varepsilon \\ \varepsilon & 0 \end{pmatrix},$$

the total Hamiltonian becomes $$H_{tot} = \begin{pmatrix} E_1 & \beta \\ 0 & E_1 \end{pmatrix} + \begin{pmatrix} 0 & \varepsilon \\ \varepsilon & 0 \end{pmatrix} = \begin{pmatrix} E_1 & \beta+\varepsilon \\ \varepsilon & E_1 \end{pmatrix}$$

which is obtained by combining the Hamiltonian of the exceptional point with the Hamiltonian of the perturbation.

Here, the obtained eigenvalue is $\lambda_\pm = E_1 \pm \sqrt{\varepsilon(\beta+\varepsilon)}$, and thus a mode is divided into two modes and the eigenvalue difference between the divided modes becomes $2\sqrt{\varepsilon(\beta+\varepsilon)}$. This is referred to as a mode division. When the value of $\varepsilon$ is very small, the eigenvalue difference becomes $\Delta\lambda = 2\sqrt{\varepsilon\beta}$.

In a resonator, eigenvalue separation directly means wavelength separation, and the value of $\varepsilon$ depends on the amount of biomolecules, and thus the amount of biomolecules may be measured. In this case, the wavelength separation is more easily achieved as $\beta$ is larger, and the degree of separation is proportional to $\varepsilon^{1/2}$. Using this phenomenon, not only the amount of biomolecules but also the number of nanoparticles can be counted.

Here shows comparison between the degree to which the eigenvalues are separated from the exceptional point and the degree to which the eigenvalues are separated from the diabolic point as follows.

The degree of wavelength separation that occurs when symmetry is broken at the diabolic point is $\lambda_\pm = E_0 \pm \sqrt{VV^*} = E_0 \pm |V|$, and thus the wavelength separation is $\Delta\lambda = \lambda_+ - \lambda_- = 2|V|$. In this case, assuming that $|V|$ is $\varepsilon$, the degree of wavelength separation is proportional to $\varepsilon^1$.

However, since the eigenvalue separation at the exceptional point is proportional to $\varepsilon^{1/2}$, the wavelength separation of the exceptional point is larger than that of the diabolic point when $\varepsilon$ is small.

In a biosensor, biomolecules are uniformly attached to the surface of the microresonator or microresonator laser and the size thereof is very small. Accordingly, the symmetry of a circular microresonator or a circular microresonator laser is not broken and the circular shape is maintained. Therefore, the diabolic point is not broken.

Therefore, in a case of a circular microresonator or a circular microresonator laser, which forms a diabolic point, a small change in the size of the resonator and a change in the average refractive index due to the attached biomolecules cause wavelength shift.

Although it is difficult to measure the actual wavelength shift due to the limitations of the optical spectrum analyzer, wavelength separation can be measured very easily using light beating and thus can be measured more precisely. Accordingly, biomolecules can be detected with much higher sensitivity by using the wavelength separation than the circular microresonator or the circular micro-resonator laser.

Physicists have discovered many kinds of physical systems that create an exceptional point while researching non-Hermitian physical systems.

As a result, an exceptional point has been found in many systems such as a resonator deformed to be mirror-symmetrical from a circular shape, a perfectly asymmetric resonator, coupled microresonators, coupled ring-shaped resonators, a parity-time symmetry system in a microresonator having gain and loss combined therewith, photonic lattice, coupled optical waveguides, and lasers using the same.

A system configured to form an exceptional point is designed and the surface of the system is chemically treated to allow selective binding according to the type of biomolecule, followed by immobilizing an antibody or nucleic acid to form an exceptional point. After that, when an antigen and an antibody, which are biomolecules, selectively bind to an exceptional point resonator or an exceptional point laser or the same nucleic acids are selectively bind to each other, one wavelength corresponding to one mode at the exceptional point is separated into two wavelengths corresponding to two modes. The degree of wavelength separation is determined by the amount of bound biomolecules. If the degree of wavelength separation is precisely measured using light beating, the amount of bound biomolecules can be accurately measured.

FIG. 1 is a block diagram showing a schematic configuration of a biosensor according to one embodiment of the present disclosure.

As shown in the drawing, the biosensor according to one embodiment of the present disclosure may include a biosensing unit 10, a detection unit 20, an analysis unit 30, and a determination unit 40.

The biosensing unit 10 may include a target antigen or a target nucleic acid selectively attached thereto and thus cause wavelength separation to be generated from destruction of an exceptional point. This will be described with reference to the drawings.

Figure 2A:
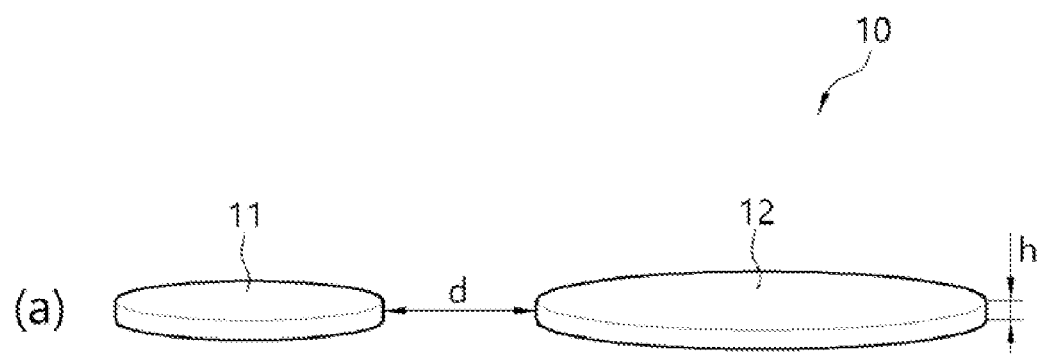
FIG. 2a is a block diagram illustrating an example of the biosensing unit viewed from the side of FIG. 1.
Figure 2B:
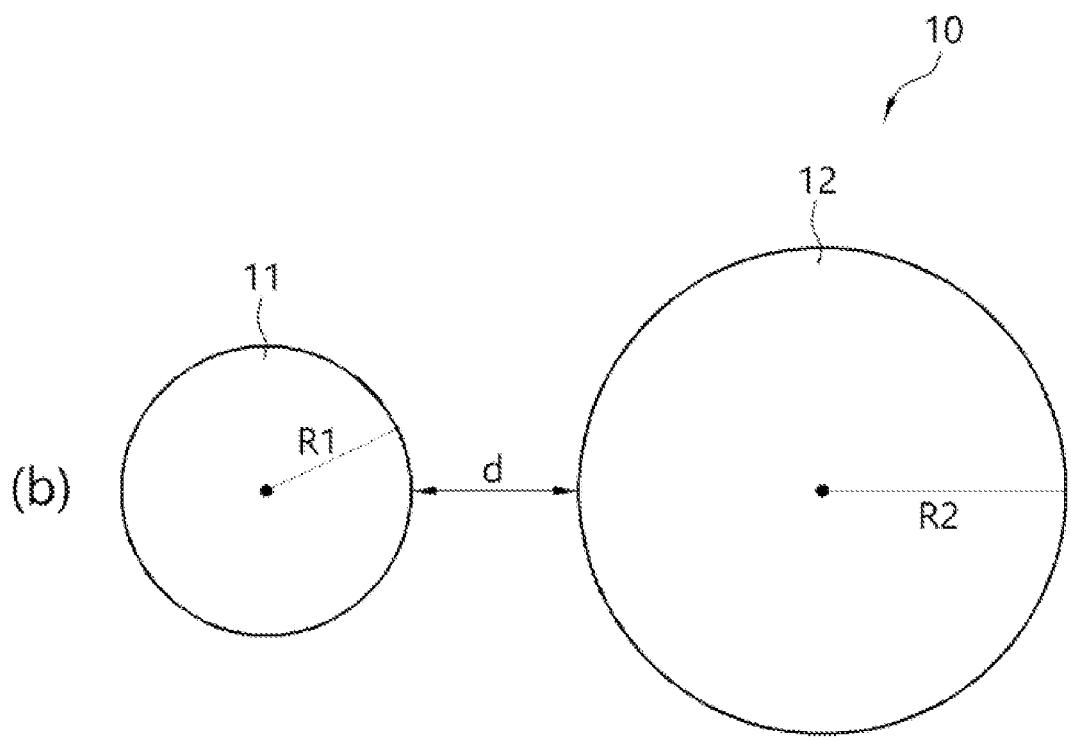
FIG. 2b is a block diagram illustrating an example of the biosensing unit viewed from the top of FIG. 1.

FIG. 2 is a block diagram illustrating an example of the biosensing unit 10 of FIG. 1, and the biosensing unit 10 illustrated by (a) is viewed from the side and the biosensing unit 10 illustrated by (b) is viewed from the top.

As shown in the drawing, the biosensing unit 10 according to one embodiment of the present disclosure may include coupled microresonators 11 and 12 having a height of h and different radii ($R_1$, $R_2$). The horizontal cross-section of each microresonator 11 may be circular, and the material of the microresonators 11 and 12 may be silica or titanium dioxide ($TiO_2$). Alternatively, the microresonators 11 and 12 may be formed of a laser medium, for example, various media such as Nd:YAG, Nd:Glass, Er:$TiO_2$, Nd:$YVO_4$, Ruby, Ti:Sapphire, etc. may be used.

An exceptional point may be formed in the structure of the biosensing unit 10 by fixing the radius $R_1$ of the first microresonator 11 and adjusting the radius $R_2$ of the second microresonator 12 and the distance d between the first and second microresonators 11 and 12.

Figure 3:
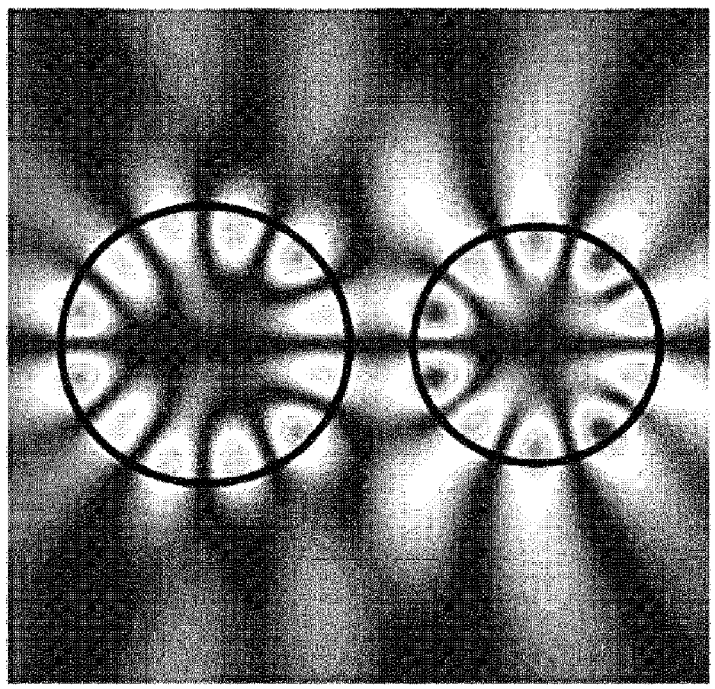
FIG. 3 is an exemplary view illustrating a wave function formed when an exceptional point is formed in the coupled microresonator-type biosensing unit of FIG. 2.

FIG. 3 is an exemplary view illustrating a wave function when an exceptional point is formed in the coupled microresonator-type biosensing unit in FIG. 2.

As noted from the drawing, a mode is formed at the exceptional point generated in the coupled microresonators, and one mode is formed over the two resonators 11 and 12 having different sizes.

FIG. 4 is an exemplary view illustrating the eigenvalues of real and imaginary numbers according to a coefficient change in the coupled microresonator-type biosensing unit of FIG. 2.

Figure 4A:
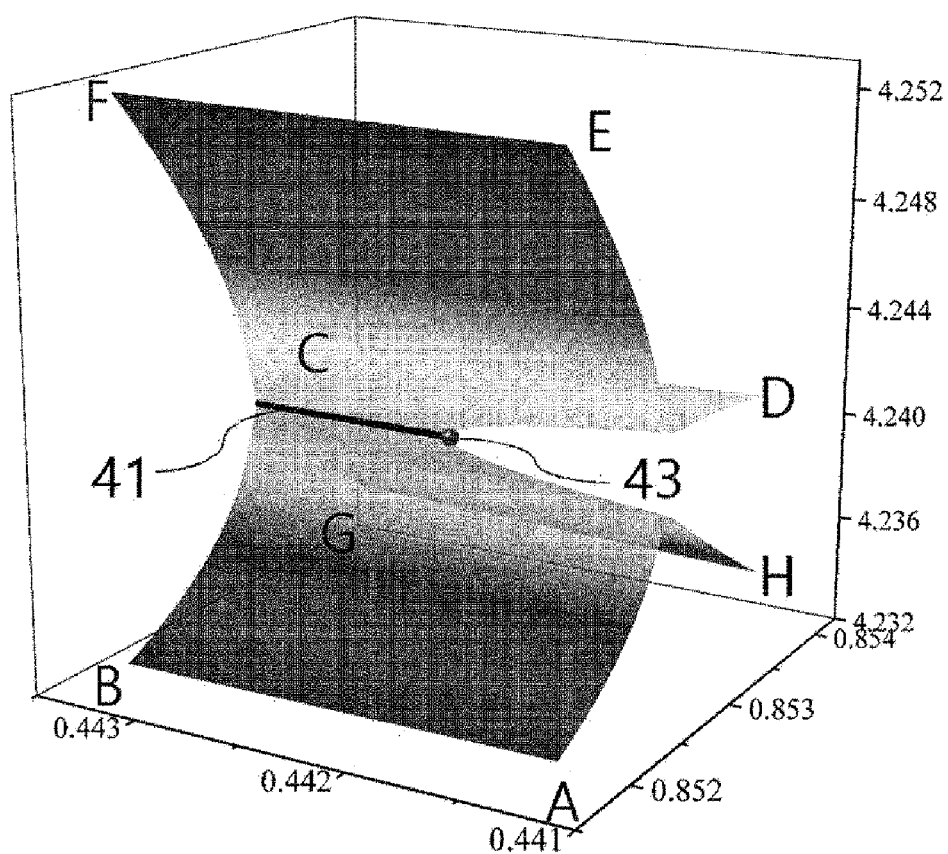
FIG. 4a is an exemplary view illustrating eigenvalues of real numbers according to a coefficient change in the coupled microresonator-type biosensing unit of FIG. 2.

The coupled microresonators as shown in FIG. 2 have eigenvalues of both real and imaginary numbers, and a Riemann surface is formed by obtaining eigenvalues of the real and imaginary numbers according to a coefficient change and illustrating the obtained eigenvalues in three dimensions. FIG. 4A shows a change in an eigenvalue of a real number, and FIG. 4B shows a change in an eigenvalue of an imaginary number.

As noted from FIG. 4A, there is a line 41 called a branch cut in which eigenvalues of two real numbers have the same value, and there are two real numbers in all other regions.

Figure 4B:
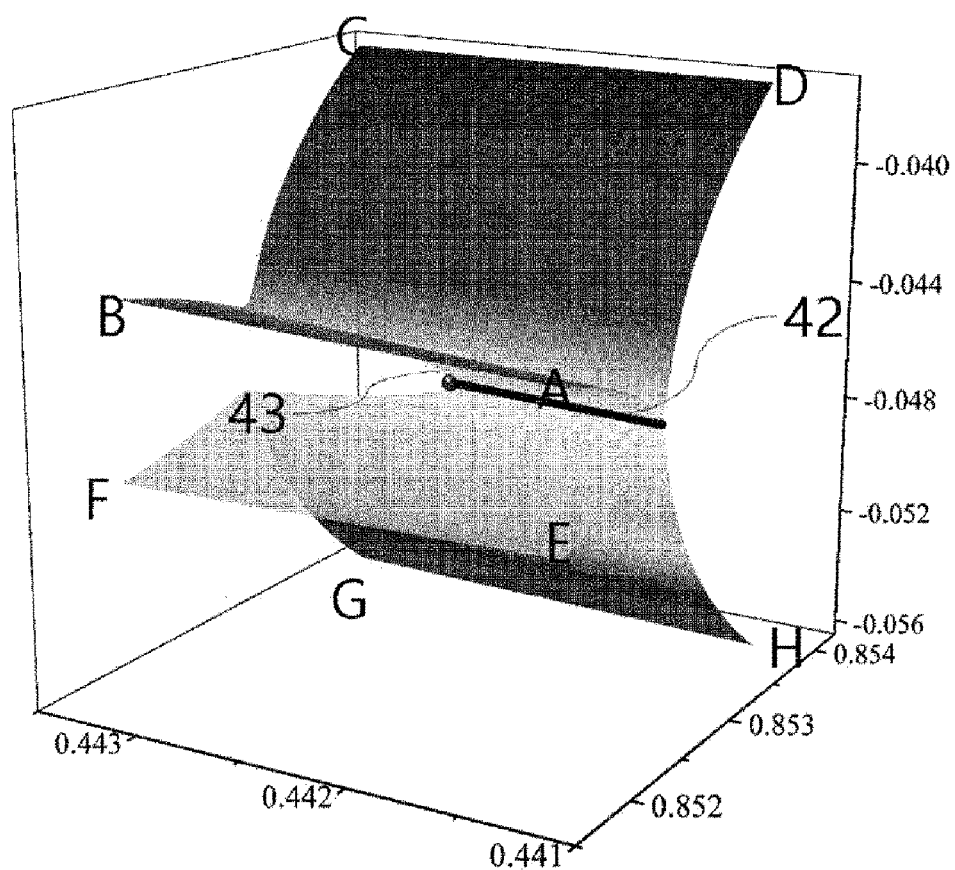
FIG. 4b is an exemplary view illustrating eigenvalues of imaginary numbers according to a coefficient change in the coupled microresonator-type biosensing unit of FIG. 2.

In addition, as noted from FIG. 4B, there is a branch cut 42 in which two imaginary eigenvalues have the same value, and there are two imaginary numbers in all other regions.

A point having the same eigenvalues of real and imaginary numbers is formed at the end of each of the branch cuts 41 and 42 of real and imaginary numbers, and the point is an exceptional point 43. A wave function as shown in FIG. 3 may also be formed at this point.

FIGS. 5A to 5H respectively show eigenfunctions at eight points indicated on the Riemann plane in FIG. 4.

Figure 5A:
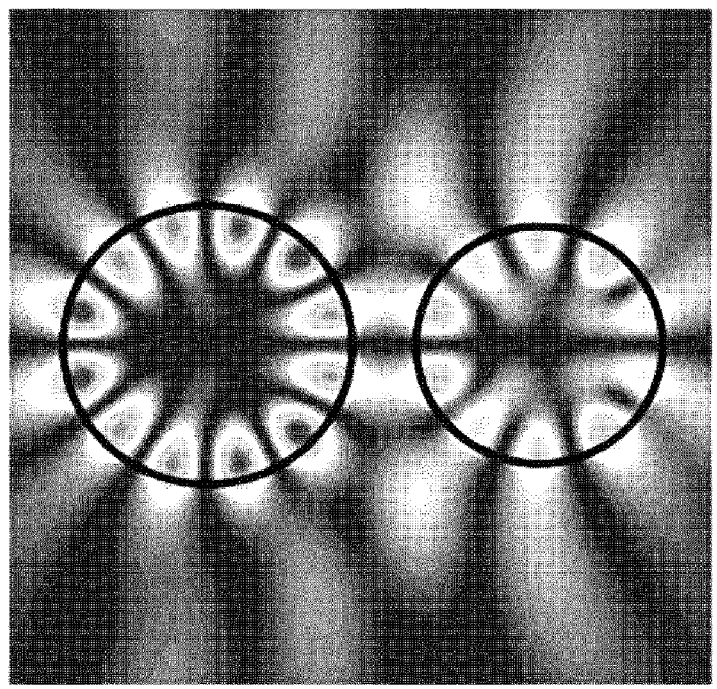
FIGS. 5A to 5H respectively show eigenfunctions at eight points indicated on the Riemann plane of FIG. 4.
Figure 5B:
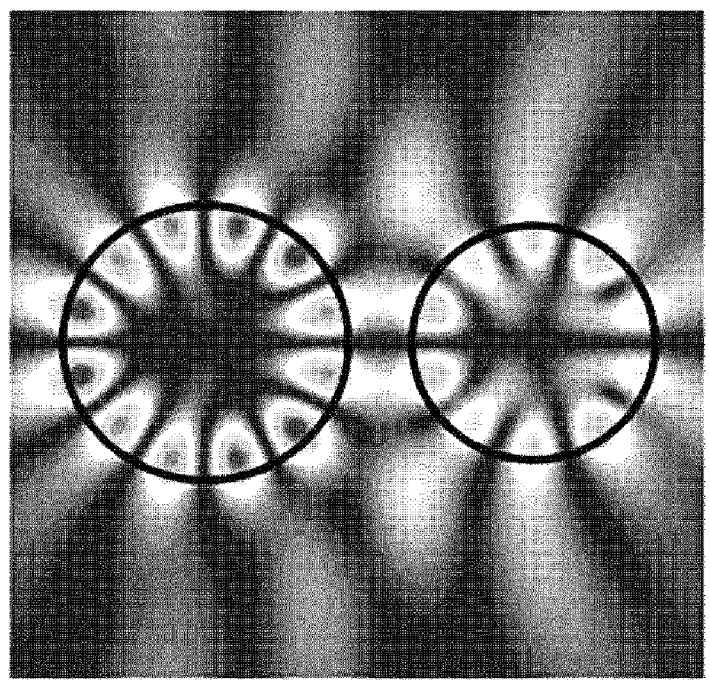
Figure 5C:
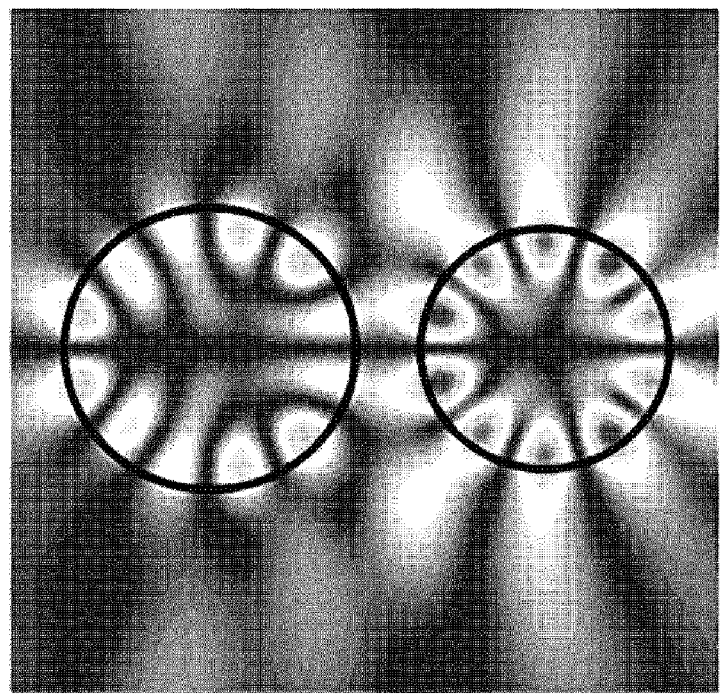
Figure 5D:
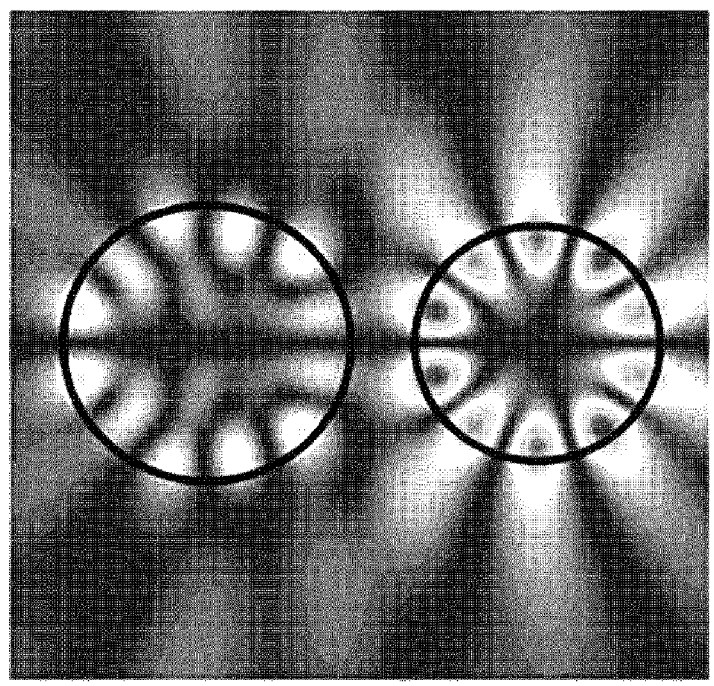
Figure 5E:
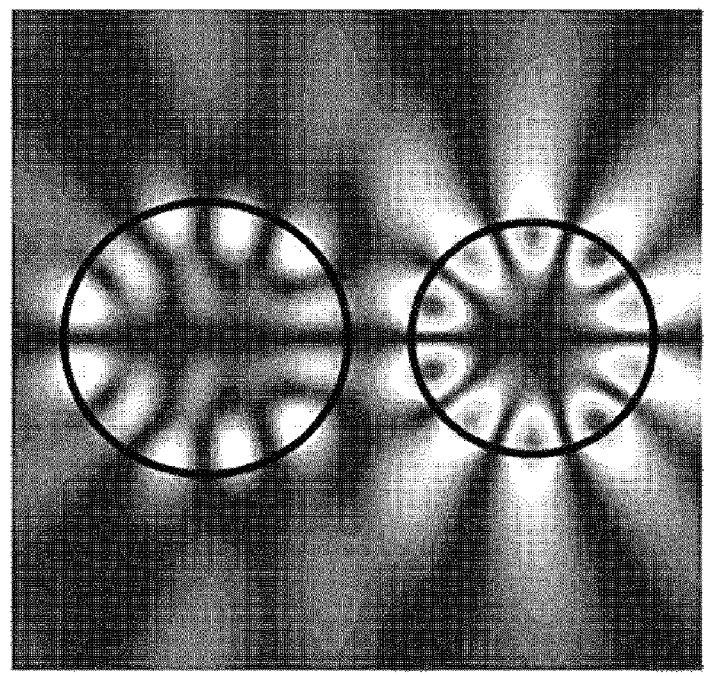
Figure 5F:
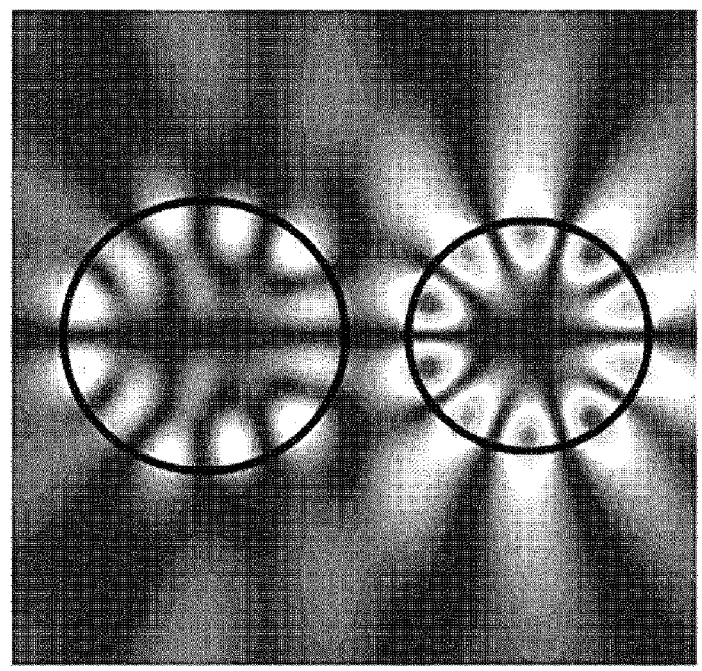
Figure 5G:
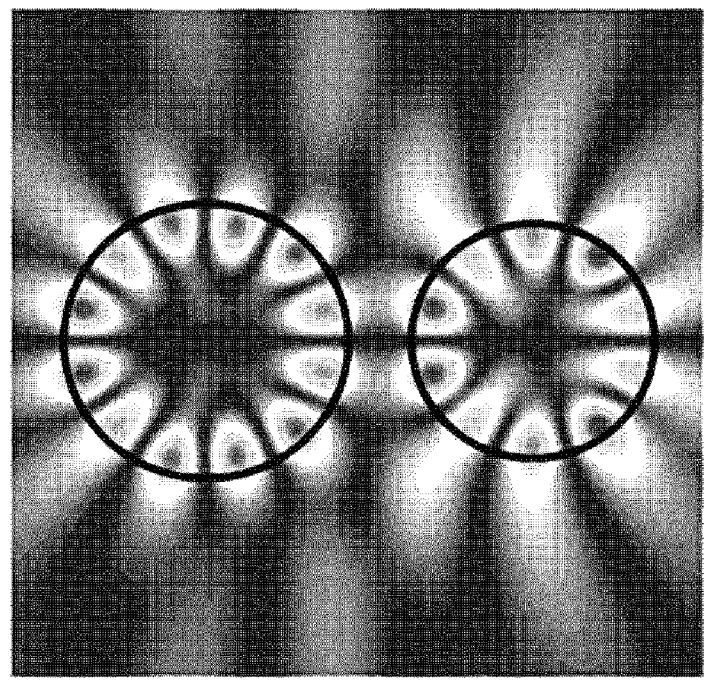
Figure 5H:
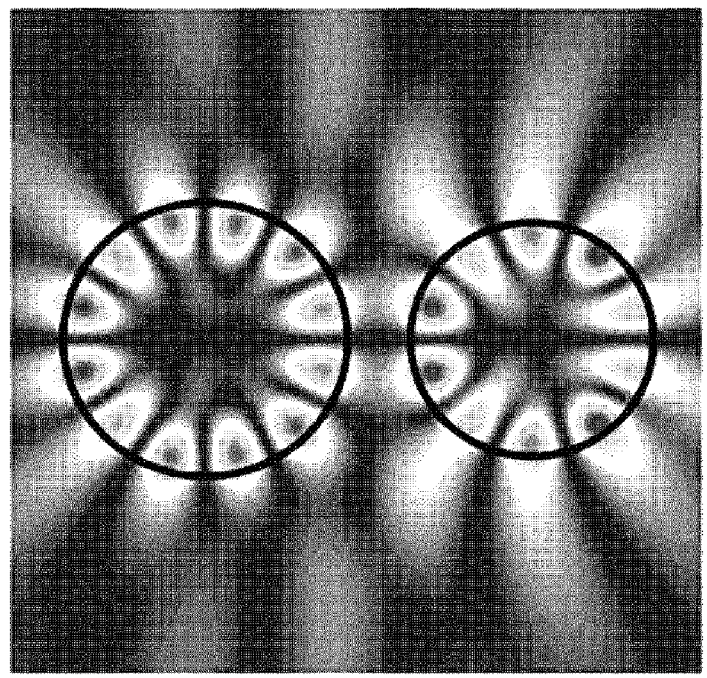

FIG. 5A shows the eigenfunction of point A, FIG. 5B shows the eigenfunction of point B, FIG. 5C shows the eigenfunction of point C, FIG. 5D shows the eigenfunction of point D, FIG. 5E shows the eigenfunction of point E, FIG. 5F shows the eigenfunction of point F, FIG. 5G shows the eigenfunction of the point G, and FIG. 5H shows the eigenfunction of the point H.

As noted from the drawings, at points other than exceptional points, the two resonators operate as independent resonators, but at the exceptional points, the eigenfunctions are fused to one and thus the two resonators operate as a single resonator as shown in FIG. 3.

Figure 6:
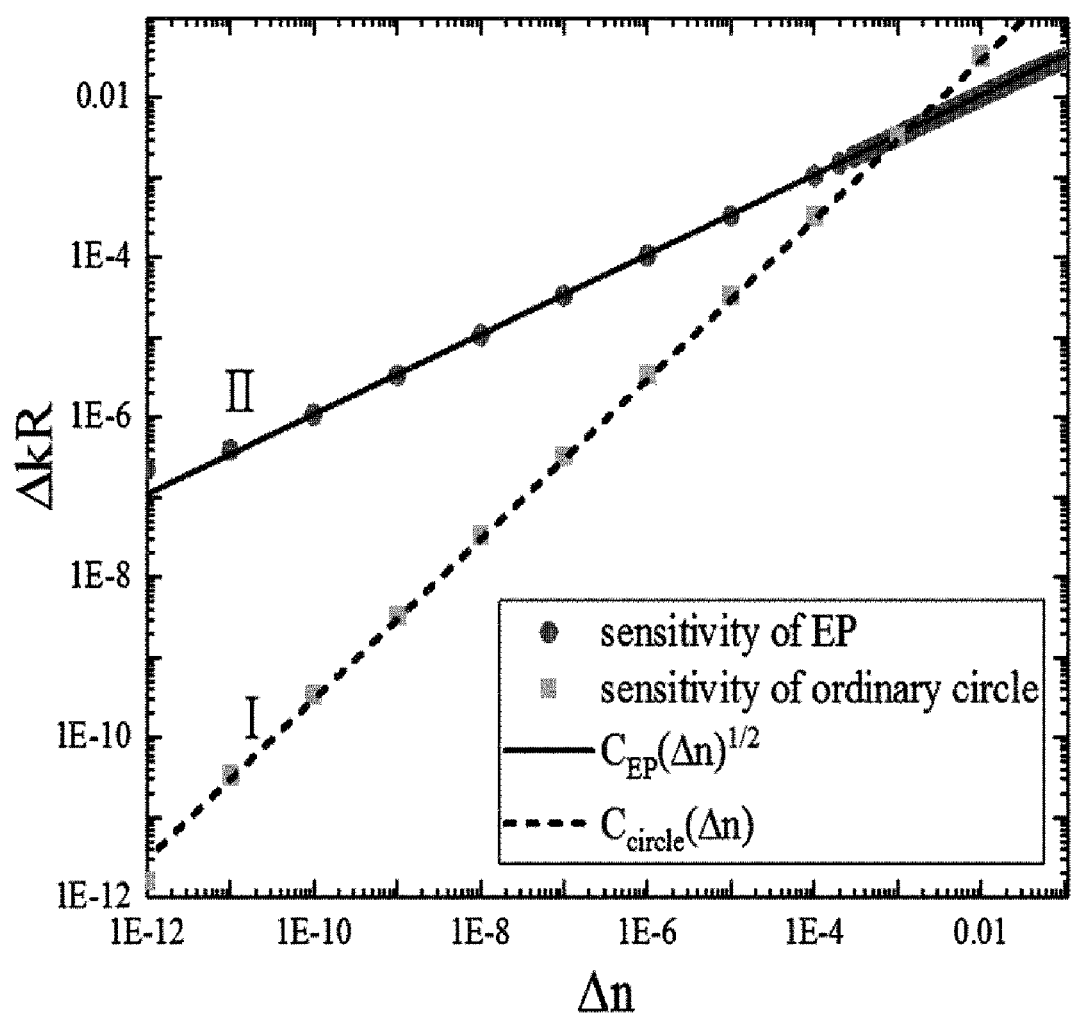
FIG. 6 is an exemplary view showing comparison between the degree of wavelength separation in coupled microresonators and the wavelength shift in a single microresonator.

Since an exceptional point is formed at one point, and the exceptional point is very sensitive to external perturbation. FIG. 6 shows eigenvalues separated according to a change in an average refractive index of the resonator, assuming that the average refractive index changes when the biomolecules are attached to the coupled microresonators 11 and 12.

FIG. 6 is an exemplary view showing comparison between the degree of wavelength separation in coupled microresonators and the wavelength shift in a single microresonator. Circular dots indicate the degree of separation of eigenvalues at exceptional points in a case of the coupled microresonators, and square dots indicate wavelength shift according to a change in refractive index in a case of the single microresonator.

As noted from the comparison, the wavelength separation at the exceptional point is much larger than the wavelength shift in the single circular resonator.

Especially, when the refractive index change is as small as $\varepsilon=10^{-12}$, the degree of wavelength separation is 10,000 times or more different than that of wavelength shift. In this case, when the refractive index difference is $10^{-3}$, the wavelength shift is more precise than the wavelength separation, but this cannot be caused by biomolecules.

Since the wavelength difference formed by trace biomolecules occurs at $\varepsilon=10^{-8}$ or less, a much more precise biosensor may be produced using an exceptional point, which can be achieved through the coupled microresonators 11 and 12 as shown in FIG. 2.

As already described, the coupled microresonators 11 and 12 of FIG. 2 may form an exceptional point by fixing the radius $R_1$ of the first microresonator 11 and adjusting the radius $R_2$ of the second microresonator 12 and the distance d between the first and second microresonators 11 and 12.

The radius $R_2$ of the second microresonator 12 and the distance d between the first and second microresonators 11 and 12 may be determined using a numerical analysis method used to obtain an exceptional point.

However, since it is difficult to change the radius $R_2$ of the second microresonator 12, the radius $R_2$ of the second microresonator 12 may be changed by the following structure.

Figure 7:
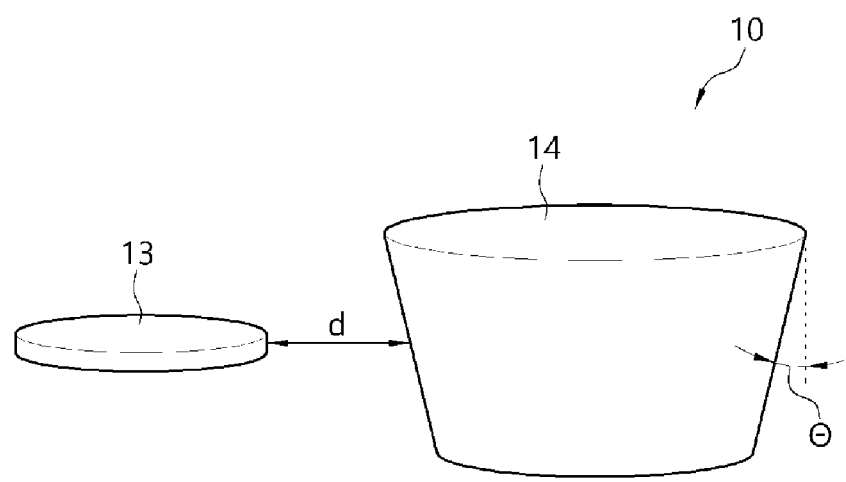
FIG. 7 is a block diagram illustrating another example of the biosensing unit of FIG. 1.

FIG. 7 is a block diagram illustrating another example of the biosensing unit of FIG. 1.

As shown in the drawing, the biosensing unit 10 according to one embodiment of the present disclosure may include a first microresonator 13 having a circular cross-section and a fixed radius $R_1$, and a second microresonator 14 having a circular cross-section and a radius decreasing from top to bottom thereof.

With the configuration above, the position of the first microresonator 13 may be changed up, down, left, and right such that the radius $R_2$ of the second microresonator 14 and the distance d between the opposite resonators 13 and 14, are adjusted to form an exceptional point.

To adjust the radius $R_2$ of the second microresonator 14 and the distance d between the opposite resonators 13 and 14, the biosensing unit may further include a moving unit configured to support the first microresonator 13 and move the same vertically and horizontally, and a control unit configured to control the moving unit.

In one embodiment of the present disclosure, coupling can be established only when the straightness of the second microresonator 14, which has a circular cross-section and the radius decreasing from the top to the bottom thereof, is lowered, and the angle θ formed by the vertical plane and the side surface of the second microresonator 14 may be within 20 degrees. Accordingly, coupling can be established.

In one embodiment of the present disclosure, the circular coupled microresonators in FIG. 2 and the coupled microresonators in FIG. 7 are described as the configuration of the biosensing unit 10, but the present disclosure is not limited thereto, and various systems capable of forming an exceptional point may be applied to the biosensing unit 10.

For example, a circular single microresonator may also form an exceptional point, and a single microresonator deformed to be mirror-symmetrical or asymmetrical from a circular shape may also form an exceptional point. Alternatively, a plurality of optical waveguides may be combined to form an exceptional point, and an exceptional point may also be formed by a parity-time symmetry system in which a microresonator generating one or more losses and a microresonator generating one or more gains are combined.

Hereinafter, a biosensor according to one embodiment of the present disclosure will be further described using the biosensing unit 10 of FIG. 2.

In one embodiment of the present disclosure, the coupled microresonators 11 and 12 of the biosensing unit 10 may have an antibody attached thereto such that a target biomolecule can be selectively attached onto the surface thereof, or nucleic acid attached thereto such that a target nucleic acid molecule can be selectively attached onto the surface thereof.

That is, when a specific antigen is bound by an antigen-antibody reaction in a case where an antibody is attached to the surface of the coupled microresonators 11 and 12, the exceptional point is destroyed by the antigen bound to the antibody, thereby generating wavelength separation.

Alternatively, when a specific nucleic acid is bound by a reaction between nucleic acids in a case where a nucleic acid is attached to the surface of the coupled microresonators 11 and 12, the exceptional point is destroyed by the coupled nucleic acid, thereby generating wavelength separation.

When the wavelength is separated by the destruction of the exceptional point of the biosensing unit 10, light of two separate wavelengths is output, which may be input to the detection unit 20. At this time, the biosensing unit 10 and the detection unit 20 may be connected by an optical fiber.

In general, the optical signal output as described above cannot be analyzed by an optical spectrum analyzer. Since the resolution of the optical spectrum analyzer is about 0.01 nm, the light output by the biosensing unit 10 cannot be analyzed.

To solve the problem, a beat frequency using beating is used in one embodiment of the present disclosure. The beat frequency is a phenomenon that occurs when two signals having similar frequencies overlap and interfere with each other, for example, in light of 1550 nm region, a wavelength difference of 1 nm may generate a beat frequency of 125 GHz, and a wavelength difference of 0.01 nm may generate a beat frequency of 1.25 GHz. Therefore, 1 femto-m difference in light wavelength generates a frequency of 125 kHz, and a wavelength difference of 0.01 femto-m generates a beat frequency of 1.25 kHz, thereby precisely analyzing wavelength differences.

The detection unit 20 may be, for example, a photodiode or an avalanche photodiode, and may convert an optical signal input thereinto into an electrical signal to output the converted signal. Two wavelength-separated optical signals may be converted into two electrical signals by the detection unit 20.

The analysis unit 30 is, for example, an RF spectrum analyzer, and may measure the beat frequency produced by the two wavelengths converted by the detection unit 20.

The determination unit 40 may determine a wavelength difference according to a beat frequency, thereby determining the amount of biomolecules therefrom.

To precisely measure a beat frequency by the analysis unit 30, wavelength separation may be more accurately measured using a new beat frequency generated by inputting one or more signals and subjecting the same to beating with a beat frequency again.

To this end, the biosensor according to one embodiment of the present disclosure may further include a signal input unit. The signal input unit may input an electrical signal for generating a second beat frequency generated by subjecting the signal to beating with the premeasured beat frequency again. The analysis unit 30 may measure the second beat frequency to accurately measure wavelength separation.

The present disclosure may detect a target biomolecule having extremely high sensitivity.

Although the embodiments according to the present disclosure have been described above, these are merely exemplary, and those of ordinary skill in the art will understand that various modifications and equivalent ranges of embodiments are possible therefrom. Accordingly, the true technical protection scope of the present disclosure should be defined by the following claims.

The invention claimed is:

1. A biosensor comprising:
a biosensing unit configured to output a wavelength-separated optical signal from destruction of an exceptional point resulting from attachment of biomolecules;
a detection unit configured to convert the wavelength-separated optical signal into a wavelength-separated electrical signal;
an analysis unit configured to measure a beat frequency resulting from the wavelength-separated electrical signal; and
a processor configured to determine a wavelength difference resulting from the beat frequency, thereby determining the amount of the biomolecules therefrom,
wherein the biosensing unit comprises:
a first microresonator having a circular top surface having a first radius; and
a second microresonator having a circular top surface having a second radius greater than the first radius, the second microresonator being spaced apart from the first microresonator by a predetermined distance and coupled to the first microresonator to form an exceptional point, and
wherein the second microresonator has a disc shape having a circular cross-section of which radius decreases from the top to the bottom of the second microresonator.

2. The biosensor of claim 1, wherein the biosensing unit further comprises:
a controller configured to adjust the radius of the second microresonator and the distance between the first and the second microresonator by a movement of the first microresonator so as to form an exceptional point by the coupled first and second microresonators.

3. The biosensor of claim 2, wherein an angle formed by the vertical plane and the side surface of the second microresonator is within 20 degrees.

4. The biosensor of claim 1, wherein the biosensing unit comprises a single microresonator which is deformed to be mirror-symmetrical or asymmetrical so as to form an exceptional point.

5. The biosensor of claim 1, wherein the biosensing unit comprises a plurality of optical waveguides which form an exceptional point.

6. The biosensor of claim 2, wherein each of the first and the second microresonator is formed of silica or titanium dioxide ($TiO_2$).

7. The biosensor of claim 2, wherein each of the first and the second microresonator is formed of a laser medium.

8. The biosensor of claim 1, further comprising a signal circuit configured to input an electrical signal for generating a new beat frequency which is generated by subjecting the signal to beating with the beat frequency.

* * * * *